(12) United States Patent
Alvarez

(10) Patent No.: US 12,416,623 B1
(45) Date of Patent: Sep. 16, 2025

(54) REAL-TIME DETECTION OF GAS KICKS DURING DRILLING AND GAS CAP GAS INTRUSION DURING OIL PRODUCTION

(71) Applicant: Saudi Arabian Oil Company, Dhahran (SA)

(72) Inventor: Jose Oliverio Alvarez, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/667,342

(22) Filed: May 17, 2024

(51) Int. Cl.
*G01N 33/28* (2006.01)
*E21B 47/113* (2012.01)
*G01N 22/00* (2006.01)

(52) U.S. Cl.
CPC ........ *G01N 33/2841* (2013.01); *E21B 47/114* (2020.05); *G01N 22/00* (2013.01); *G01N 33/2823* (2013.01)

(58) Field of Classification Search
CPC ............... G01N 33/2841; G01N 22/00; G01N 33/2823; E21B 47/114
See application file for complete search history.

(56) References Cited

U.S. PATENT DOCUMENTS

| | | | |
|---|---|---|---|
| 3,498,112 A | 3/1970 | Howard | |
| 3,681,684 A | 8/1972 | Busker et al. | |
| 3,815,019 A | 6/1974 | Wiles | |
| 4,423,623 A | 1/1984 | Ho et al. | |
| 5,014,010 A | 5/1991 | Helms et al. | |
| 5,331,284 A | 7/1994 | Jean et al. | |
| 5,351,521 A | 10/1994 | Cracknell | |
| 5,455,516 A | 10/1995 | Jean et al. | |
| 6,826,964 B2 * | 12/2004 | Nyfors | G01N 22/00 73/861.04 |
| 6,865,926 B2 | 3/2005 | O'Brien et al. | |

(Continued)

FOREIGN PATENT DOCUMENTS

| | | |
|---|---|---|
| CN | 102721709 | 10/2012 |
| CN | 105247353 | 1/2016 |

(Continued)

OTHER PUBLICATIONS

Gao et al., "The effect of slurry concentration on coal pitch water slurry rheological properties," 2013 International Conference on Materials for Renewable Energy and Environment, Chengdu, China, 2013, 3 pages.

(Continued)

*Primary Examiner* — Crystal J Lee
(74) *Attorney, Agent, or Firm* — Fish & Richardson P.C.

(57) ABSTRACT

A method of detecting an increase in gas content in a pipe. The method includes flowing fluid through the pipe. The method includes generating, by a network analyzer, microwaves data representing a complex scattering coefficient over a first spectrum of microwave frequencies that are emitted through a waveguide and a fluid within the pipe and determining a statistical profile of a complex scattering magnitude over a second spectrum of microwave frequencies. The method includes determining that an amount of gas within the pipe satisfies a threshold amount and causing a flow of fluids within the pipe to slow or stop until the amount of gas falls below a predetermined threshold value.

20 Claims, 8 Drawing Sheets

(56) References Cited

U.S. PATENT DOCUMENTS

| | | |
|---|---|---|
| 7,345,622 B2 | 3/2008 | Edvardsson |
| 7,621,171 B2 | 11/2009 | O'Brien |
| 7,712,380 B2 | 5/2010 | Xie |
| 7,908,930 B2 | 3/2011 | Xie et al. |
| 8,224,588 B2 | 7/2012 | Wee |
| 8,794,062 B2 | 8/2014 | DiFoggio et al. |
| 8,916,815 B2 | 12/2014 | Xie et al. |
| 8,986,922 B1 | 3/2015 | Wach |
| 9,528,780 B2 | 12/2016 | Wray et al. |
| 10,739,494 B2 | 8/2020 | Thompson et al. |
| 10,865,640 B2 | 12/2020 | Alvarez |
| 10,920,579 B2 | 2/2021 | Beaman, Jr. et al. |
| 11,156,079 B2 | 10/2021 | Alvarez |
| 11,460,416 B2 | 10/2022 | Alvarez et al. |
| 11,709,141 B2 | 7/2023 | Alvarez |
| 2004/0244501 A1 | 12/2004 | Nyfors et al. |
| 2007/0085729 A1 | 4/2007 | Edvardsson |
| 2007/0279073 A1 | 12/2007 | Wee |
| 2008/0295609 A1 | 12/2008 | Xie |
| 2008/0319685 A1 | 12/2008 | Xie et al. |
| 2009/0088985 A1 | 4/2009 | Wee |
| 2010/0270291 A1 | 10/2010 | Kotzian et al. |
| 2011/0098938 A1 | 4/2011 | Huang et al. |
| 2013/0110411 A1 | 5/2013 | Black et al. |
| 2014/0090451 A1 | 4/2014 | Surman et al. |
| 2015/0148919 A1* | 5/2015 | Watson .................. G06N 5/043 700/31 |
| 2015/0218941 A1 | 8/2015 | Clarke et al. |
| 2016/0161425 A1* | 6/2016 | Berezin .............. G01N 33/2823 324/638 |
| 2016/0334343 A1 | 11/2016 | Hurlimann et al. |
| 2017/0059492 A1 | 3/2017 | Karimi et al. |
| 2017/0191977 A1 | 7/2017 | Nyfors |
| 2017/0248530 A1 | 8/2017 | Parker et al. |
| 2019/0047865 A1 | 2/2019 | Zeller et al. |
| 2020/0190970 A1* | 6/2020 | Alvarez ................... E21B 47/13 |
| 2021/0173111 A1* | 6/2021 | Therrien ............... E21B 47/113 |
| 2022/0346198 A1 | 10/2022 | King et al. |

FOREIGN PATENT DOCUMENTS

| | | |
|---|---|---|
| EP | 0372843 | 6/1990 |
| EP | 0637377 | 2/1995 |
| EP | 1451562 | 9/2004 |
| EP | 1926991 | 6/2008 |
| GB | 2110377 | 6/1983 |
| GB | 2430493 | 3/2007 |
| JP | H11118733 | 4/1999 |
| JP | 2001083102 | 3/2001 |
| JP | 2004046044 | 2/2004 |
| JP | 2008032528 | 2/2008 |
| JP | 2012073255 | 4/2012 |
| RU | 2594338 | 8/2016 |
| WO | WO 2007043950 | 4/2007 |
| WO | WO 2007129901 | 11/2007 |
| WO | WO 2014027322 | 2/2014 |
| WO | WO 2014177707 | 11/2014 |

OTHER PUBLICATIONS

Holmes et al., "Monitoring Water Contamination in Jet Fuel Using Silica-Based Bragg Gratings," IEEE Sensors Journal, Apr. 2019, 19(8):2984-2990, 6 pages.

Hong et al., "Numerical Model for Uniform Microwave-Assisted Continuous Flow Process of Biodiesel Production," 2018 International Conference on Microwave and Millimeter Wave Technology, Chengdu, China, 2018, 3 pages.

Karimi et al., "Design and Dynamic Characterization of an Orientation Insensitive Microwave Water-Cut Sensor," IEEE Microwave Theory and Technique, Jun. 2017, 11 pages.

Ren, "The influence by temperature and product density to accuracy of magnetostrictive level gauge," International Conference on Information Acquisition, 2004 Proceedings, Hefei, China, 2004, 4 pages.

Tan et al., "Wireless Underground Sensor Networks: MI-based communication systems for underground applications," IEEE Antennas and Propagation Magazine, Aug. 2015, 57(4):74-87, 14 pages.

Videira et al., "Introducing novel light management to design a hybrid high concentration photovoltaic/water splitting system," 2015 IEEE 42nd Photovoltaic Specialist Conference (PVSC), New Orleans, LA, Jun. 2015, 6 pages.

* cited by examiner

REAL-TIME DETECTION OF GAS KICKS DURING DRILLING AND GAS CAP GAS INTRUSION DURING OIL PRODUCTION

TECHNICAL FIELD

The present disclosure applies to techniques for wellbore drilling, such as for hydrocarbon extraction. More specifically, the present disclosure relates to techniques for detecting gas kicks during drilling and gas cap gas intrusion during oil production.

BACKGROUND

In an oil and gas production operation, fluid containing hydrocarbons are produced from a reservoir and transported within a hydrocarbon production pipe. The fluid can include oil, gas, and water. During a wellbore drilling operation, an oil-based drilling mud is transported through the wellbore for lubrication, cuttings removal, and other processes related to drilling the wellbore. The oil-based drilling mud is returned through a mud return pipe and re-circulated to the wellbore. An amount of gas contained in the drilling mud is closely monitored to determine a risk of a gas kick, or a sudden influx of gas into the drilling mud.

SUMMARY

This specification describes techniques that can be used for detecting gas kicks in real-time during drilling and gas cap gas intrusion during hydrocarbon production. Gas kicks are increases in a gas volume fraction (GVF) of a fluid transported with a hydrocarbon production pipe or mud return pipe. Gas cap intrusion is an intrusion of gas from the uppermost part of a hydrocarbon reservoir into a production region where hydrocarbons are extracted during hydrocarbon production. If left unmonitored, gas kicks can be destructive events during drilling. The technique described in this specification relates to an automated monitoring of increases in GVF that is sensitive to small changes in GVF. The techniques can result in an early detection of gas in a fluid within a pipe which can trigger an alerting of personnel in the field and/or initiation of mitigation actions including changing the composition of drilling mud, gas kick containment processes (e.g., implementing a mud-gas separation process), and/or other mitigating actions.

An analysis of electromagnetic properties of fluid transported with a pipe is a non-invasive approach to observe the contents of the fluid. For example, different fluids exhibit different electric permittivity, which leads to varying reflection and transmission coefficients of incident electromagnetic waves. The fluid transported with the pipe is often an oil-based mud (OBM) or water-based mud (WBM) in the case of a mud return pipe. The fluid transported with the pipe is often a hydrocarbon or oil and gas mixture in the case of a hydrocarbon production pipe. The electromagnetic properties of oil and gas are similar. The techniques described in this specification can electromagnetically distinguish between a fluid (e.g., an OBM fluid) with a high gas content and a fluid with a low gas content to effectively provide an early detection of an oncoming increase in gas content.

Implementations of the systems and methods of this disclosure can provide various technical benefits. Early, automated, and non-invasive detection of increases in gas content in a pipe during drilling and hydrocarbon extraction can be achieved by monitoring one or more parameters of a statistical profile (e.g., a bimodality coefficient, variance, etc.) of microwave transmission measurements. Although the electromagnetic response of a fluid with a high gas content is similar to the electromagnetic response of a fluid with a low gas content, the shape of the statistical profile is indicative of an amount of gas present in the fluid. By monitoring the shape of the statistical profile through the one or more parameters, a system can detect small increases in gas content early and trigger one or more mitigation strategies and/or alerting protocols to avoid a potentially dangerous and/or destructive gas kick event.

Aspects of the previously described implementation are implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The details of one or more implementations of these systems and methods are set forth in the accompanying drawings and the description below. Other features, objects, and advantages of these systems and methods will be apparent from the description and drawings, and from the claims.

DESCRIPTION OF DRAWINGS

Like reference numbers and designations in the various drawings indicate like elements.

DETAILED DESCRIPTION

Figure 1:
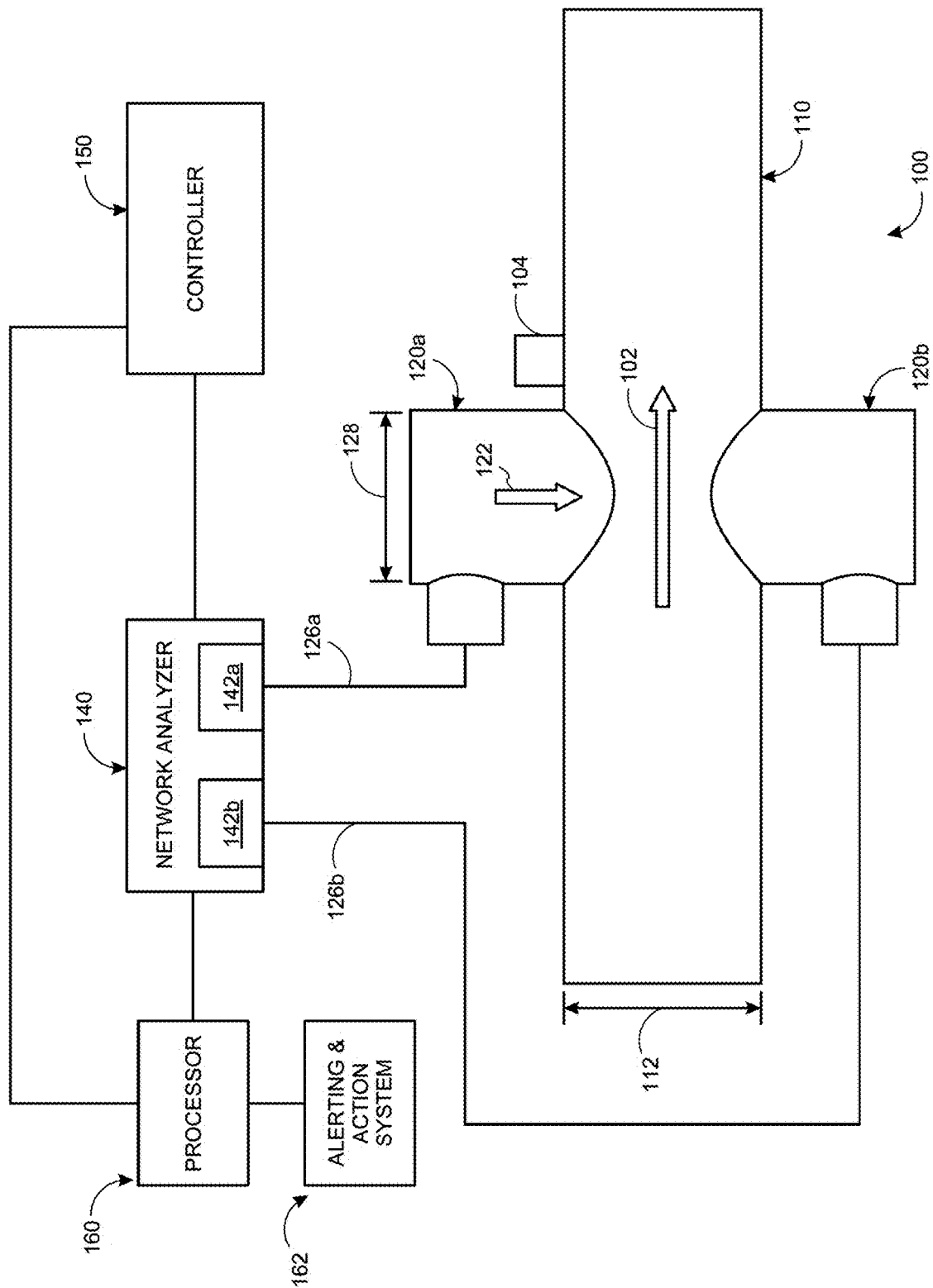
FIG. 1 is an example schematic of a microwave sensing apparatus to monitor the contents of a pipe.

This specification describes techniques that can be used for detecting an increase in gas content (e.g., a gas kick) in a pipe during the drilling of a wellbore into a reservoir for hydrocarbon extraction or in a pipe during the production of hydrocarbons from a reservoir. Gas kicks are increases in a GVF of a fluid transported with pipe (e.g., a hydrocarbon production pipe, drilling mud return pipe, etc.) during drilling or hydrocarbon extraction. If left unmonitored, gas kicks can be destructive events. The technique described relates to an automated monitoring of increases in GVF that is sensitive to small changes in GVF. The techniques can result in an early detection of a likely gas kick which can trigger an alerting of personnel in the field and/or initiation of mitigation actions including changing the composition of drilling mud, gas kick containment processes (e.g., implementing a mud-gas separation process), and/or other mitigating actions.

In addition to early detection of gas kicks, the described techniques can be used for detecting gas cap gas intrusion during hydrocarbon production. In some cases, extracting hydrocarbons from reservoirs with a large gas cap (e.g., gas located at the uppermost section of the reservoir) consists of producing hydrocarbons in a zone below the gas cap region first and delaying production from the gas cap zone until other regions are depleted. During hydrocarbon production, gas from the gas cap can intrude into the reservoir.

In some cases, premature hydrocarbon production from the gas cap zone affects the planned extraction of hydrocarbons from the reservoir. When the gas/oil ratio (GOR) increases, production facilities must be ready to handle the large amount of gas. The gas is reinjected into the reservoir through new wells, and gas storage and injection equipment must be acquired. In addition, early hydrocarbon production in the gas cap region can cause a stripping of asphaltene from oil and cause asphaltene precipitation in high GOR wells.

An analysis of electromagnetic properties of fluid transported with a pipe is a non-invasive approach to observe the contents of the fluid. For example, different fluids exhibit different electric permittivity, which leads to varying reflection and transmission coefficients of incident electromagnetic waves. The fluid transported with the pipe during drilling is often an OBM with a percentage of gas (e.g., methane) contained in the fluid as well. The fluid transported with the pipe during hydrocarbon extraction is often a mixture of oil and gas. The electromagnetic properties of oil and gas are similar. The techniques described in this specification can electromagnetically distinguish between a fluid (e.g., an OBM fluid) with a high gas content and a fluid with a low gas content to effectively provide an early detection of an oncoming gas kick. Similarly, the techniques can be used to distinguish between hydrocarbon production with no gas and hydrocarbon production with gas content from the gas cap of the reservoir.

In some cases, waveguides can be used to direct microwaves through the fluid in the pipe. The microwave can propagate through the fluid or be reflected or absorbed by the fluid. The transmitted or reflected microwaves can be analyzed, as described in the present specification, to determine one or more properties of the fluid (e.g., an estimated gas volume fraction of the fluid). In some implementations, the waveguides are dielectrically-filled waveguide. In some implementations, the waveguides are ridged waveguides. In some other implementations, the waveguides are not ridged waveguides.

FIG. 1 is a schematic diagram that illustrates an example GVF measurement system 100. The example system 100 includes waveguides 120a and 120b that are attached to a pipe 110. In some implementations, the pipe 110 is a mud return pipe. In some other implementations, the pipe 110 is a hydrocarbon production pipe. A network analyzer 140 is connected with the waveguides 120a and 120b. The network analyzer 140 is communicatively coupled with a controller 150 and a processor 160. In some implementations, the controller 150 is communicatively coupled with the processor 160.

The controller 150 determines the frequency of the microwaves emitted through the waveguides 120a and 120b and a direction of propagation of an incident microwave field. The controller 150 can configure the network analyzer 140 to emit a particular microwave frequency for a particular time period, and the controller 150 can communicate the particular frequency and the particular time period to the processor 160. In some implementations, the processor 160 includes one or more processors that are located local to the network analyzer 140 and/or the pipe 110. In some other implementations, the processor 160 includes one or more remote processors communicatively coupled to the network analyzer 140 and/or the controller.

In the oil and gas industry, a mud return pipe, for example the pipe 110, can refer to a pipe that transports a drilling mud that is used for lubrication, cuttings removal, and in some cases, to turn a drill bit. The pipe 110 can be constructed using carbon steel. The pipe 110 can also be used to transport drilling mud between other endpoints in a drilling system, either on-site or off-site. The fluid 102 can include a mixture of oil, gas, water, and drilling mud. As illustrated, the pipe 110 has a diameter 112.

Electromagnetically, materials such as fluid mixtures and OBMs are characterized by two parameters: a permittivity and a magnetic permeability. For most materials, including downhole fluid mixtures in the pipe 110, the magnetic permeability remains constant, while the permittivity varies as a function of frequency, temperature, and concentration of a particular component (e.g., gas, water, oil, mud, etc.). The permittivity can be represented as a complex value, where the real part of the complex value is related to the capacitive properties of the material, and the imaginary part of the complex value is related to different loss mechanisms in the material. In some cases, the permittivity of gas is similar to the permittivity of crude oil and many OBMs, which makes it difficult to differentiate between fluid mixtures that contain various amounts of crude oil or OBM and gas by directly observing parameters directly related to the permittivity of the fluid mixture.

The network analyzer 140 is a network analyzer that is configured to measure the magnitude and phase of S parameters of an electrical network. In some implementations, the network analyzer 140 can be a vector network analyzer (VNA). The S parameters, also referred to as the scattering parameters or the s-parameters, describe the electrical behavior of linear electrical networks when undergoing various steady state stimuli by electrical signals. The permittivity of a material can be measured by sending electromagnetic waves through it and computing the S parameters. In the illustrated example, the network analyzer 140 can measure the magnitudes and the phase of the S parameter through reflections and transmissions of microwaves. In some implementations, the network analyzer 140 includes one or more sets of transmitters and receivers. Each transmitter and receiver can include amplifiers, filters, and other electronic components that are configured to transmit or receive electronic signals.

The network analyzer 140 includes ports 142a and 142b. Each of the ports 142a and 142b can be used as an interface to connect to the electronic network to be measured. In the illustrated example, a cable 126a connects the waveguide 120a to the port 142a; and a cable 126b connects the waveguide 120b to the port 142b. The cable 126a and 126b can be coaxial cables, fiber optical cables, or other media that can be used to transmit microwaves. In an example operation, the network analyzer 140 can generate electronic signals. The electronic signals are electromagnetic waves having amplitudes and phases. In one example, the electromagnetic waves can be microwaves, having frequencies between 300 Megahertz (MHz) and 300 Gigahertz (GHz). The electromagnetic waves can be transmitted from the port 142a and propagate over the cable 126a to reach the waveguide 120a. In the illustrated example, the electromagnetic wave is referred to as microwave 122. In some cases, the microwave 122 can further propagate to the waveguide 120b over the fluid 102. The propagated signal can be received at the port 142b through the cable 126b. Alternatively, or additionally, the microwave 122 can reflect from the fluid 102 and the reflected signal can be received at the port 142a over the cable 126a. The S parameters measurements of the propagated signal and the reflected signal can be used to determine the permittivity of the fluid 102.

The S parameters include four matrix elements, each element corresponding to a particular response of the electrical circuit that is excited by an input voltage (in this case, the input voltage is a microwave excitation (e.g., microwave 122) initiated by the network analyzer 140). The four matrix elements include $S_{11}$, $S_{12}$, $S_{21}$, and $S_{22}$. The $S_{11}$ parameter corresponds to a reflection coefficient of an input signal. The $S_{12}$ parameter corresponds to a reverse gain of the input signal. In other words, the $S_{12}$ parameter describes a transmission coefficient of a signal that propagates from the output to the input (e.g., from waveguide 120b to waveguide 120a). The $S_{21}$ parameter corresponds to a forward gain of the input signal. In other words, the $S_{21}$ parameter describes a transmission coefficient of a signal that propagates from the input to the output (e.g., from waveguide 120a to waveguide 120b). The $S_{22}$ parameter corresponds to a reflection coefficient of a signal that propagates from the output to the input of the circuit. In some cases, each S parameter is a complex coefficient having a real part and an imaginary part.

In some implementations, the network analyzer 140 includes four electrical outputs, in which each electrical output corresponds to one of the four S parameters. The network analyzer 140 compares the magnitude and phase of the incoming microwave signal with the magnitude and phase of the outgoing microwave signal to determine the complex values of the S parameters.

The waveguides 120a and 120b have a diameter 128. In some implementations, the diameter 128 of the waveguides 120a and 120b are substantially similar to the diameter 112 of the pipe 110. In some implementations, the diameter of the pipe 110 is chosen based on the cutoff frequencies of different propagating modes. The waveguides 120a and 120b can be filled with a dielectric like quartz, borosilicate glass, sapphire or Noryl (a type of resin).

In a pipe such as the pipe 110, there are two kinds of propagating modes or traverse modes for electromagnetic waves to propagate through: the transverse electric (TE) and transverse magnetic (TM) modes. In a TE mode, there is a magnetic field along the direction of propagation but there is no electric field in the direction of propagation. In a TM mode, there is an electric field along the direction of propagation but there is no magnetic field in the direction of propagation. The propagation of the electromagnetic waves in the pipe can be characterized by the Maxwell's equations, which yield multiple solutions. Each solution can be represented as a propagation sub mode, denoted as $TE_{11}$, $TE_{12}$, $TM_{01}$, $TM_{11}$. The cutoff frequency for a particular mode or sub mode represents the frequency below which there is no propagation of that particular mode or sub mode. For the sub modes in the TM mode, $TM_{01}$ has the lowest cutoff frequency. For the sub modes in the TE mode, $TE_{11}$ has the lowest cutoff frequency.

In some implementations, the network analyzer 140 is communicatively coupled to a processor 160. The processor 160 receives data from the network analyzer 140 and performs one or more analyses. In some implementations, the processor 160 performs the one or more analyses that result in one or more safety signals (e.g., a detection of an oncoming gas kick). In the case of an analysis that results in one or more safety signals, an alerting and action system 162 that is communicatively coupled to the processor 160 receives a safety signal and initiates an alerting procedure and/or an action sequence. In some implementations, the alerting procedure includes notifying one or more field personnel with the corresponding analysis and safety signal. In some cases, the safety signal is one or more measured or calculated parameters that exceed a threshold value. In some implementations, the action sequence includes gas kick mitigation procedures or actions that modify the contents of the OBM in the case of a mud return line.

In some implementations, the gas volume fraction measurement system 100 is placed as part of a surface production pipe. In some other implementations, it is placed as part of a mud return pipe.

Figure 2:
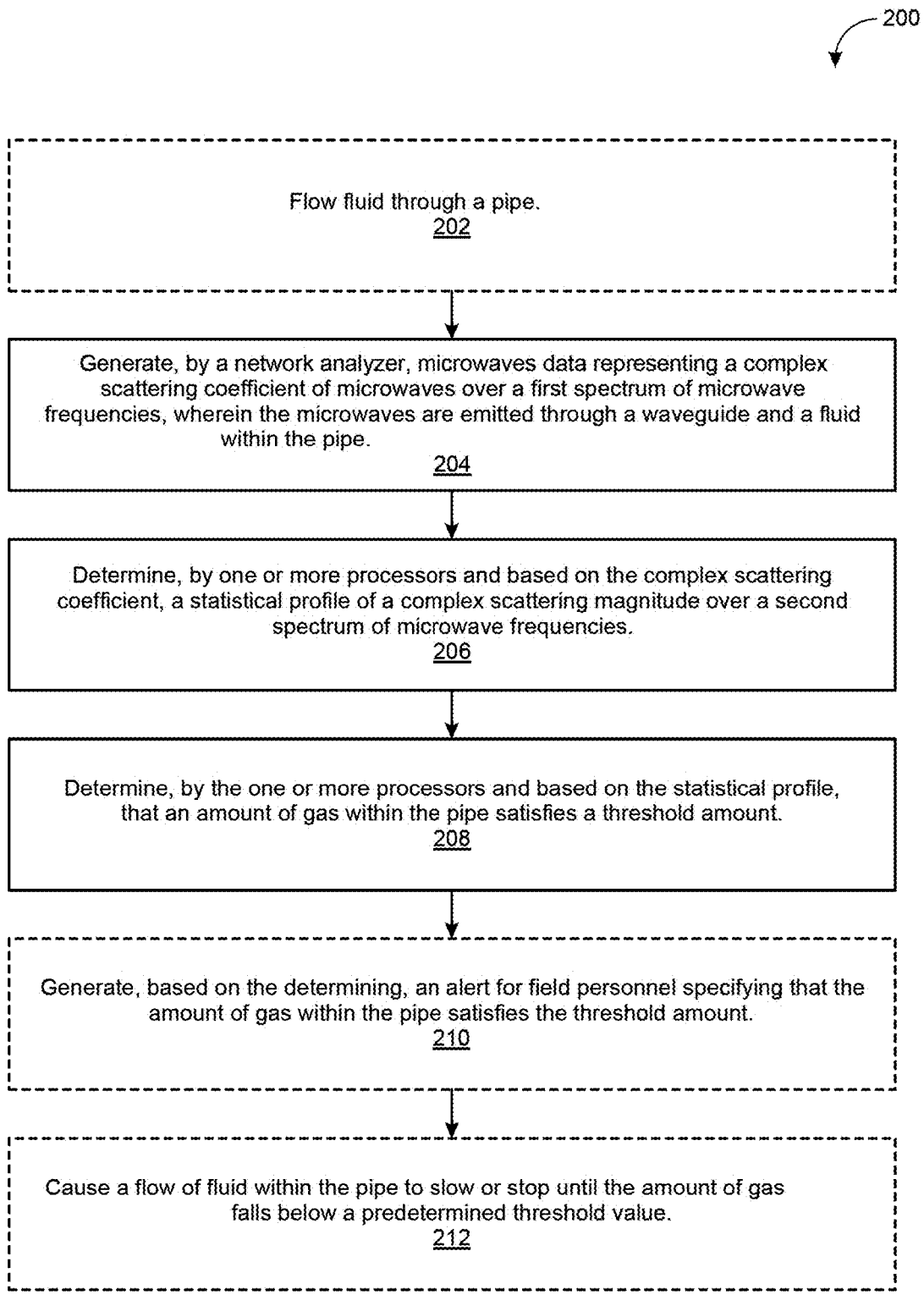
FIG. 2 is a block diagram showing an example process for monitoring contents of a pipe for an increase in gas content.

FIG. 2 is a flow diagram showing an example process 200 for monitoring a pipe for an increase in gas content, e.g., a gas kick. For clarity of presentation, the description that follows generally describes process 200 in the context of the gas volume fraction measurement system 100. In some implementations, various steps of process 200 can be run in parallel, in combination, in loops, or in any order.

In some implementations, the process 200 includes a system that flows (202) fluid through the pipe. In some cases, the fluids include hydrocarbons, oil, gas, water, drilling mud, and other fluids. In some cases, the fluids include an OBM. The pipe can connect a to a storage facility and flows one or more fluids from the wellhead to the storage facility, where the storage facility can include equipment for analysis, filtering, and storage of the fluids. In some cases, the pipe is a mud return pipe. In some cases, the pipe is a hydrocarbon production pipe. In some cases, the pipe is part of a closed loop that circulates and filters drilling mud during drilling to a reservoir.

The process 200 includes a system that generates (204), by a network analyzer (e.g., the network analyzer 140), microwaves data representing a complex scattering coefficient of microwaves (e.g., microwave 122) over a first spectrum of microwave frequencies, wherein the microwaves are emitted through a waveguide (e.g., waveguides 120a-b) and a fluid within the pipe (e.g., pipe 110). A given complex scattering coefficient can be indicative of reflection or transmission of an incident microwave signal.

In some implementations, the network analyzer is communicatively coupled to a controller (e.g., the controller 150). The controller can configure the network analyzer to emit microwaves at a particular range of frequencies for an amount of time. In addition, the controller 150 can configure the network analyzer to evaluate one or more of the S parameters as a function of microwave frequency through a measurement of the microwave fields at an end of the waveguide 120a or the waveguide 120b. In some cases, the controller can configure the network analyzer to perform multiple measurements associated with each frequency in the first spectrum of microwave frequencies.

In some implementations, the controller configures the network analyzer to evaluate a microwave transmission or reflection spectrum associated with the contents of the pipe over a first spectrum of microwave frequencies. The microwave transmission spectrum is represented by the S parameter $S_{12}$ (or $S_{21}$, depending on the direction of propagation of the microwave signal).

The controller can determine the first spectrum of microwave frequencies, e.g., a frequency band between 1 GHz and 4 GHz.

The network analyzer generates the microwaves within the pre-determined first spectrum. The microwaves are guided by a first waveguide on a first side of the pipe, through the contents of the pipe, and guided by a second waveguide on a second side of the pipe. In some implementations, the first waveguide is positioned opposite the second waveguide. In some other implementations, the first waveguide is positioned offset the second waveguide. In some cases, the content of the pipe is an oil and gas mixture. In some cases, the evaluation of the transmission spectrum by the network analyzer is performed during drilling into a reservoir.

In some implementations, the waveguides are dielectrically-filled waveguides. In some cases, the waveguides are ridged waveguides. In some other cases, the waveguides are non-ridged waveguides.

In some implementations, the network analyzer transmits electrical signals to one or more processors, which can save, analyze, and monitor the collected measurements.

The process 200 includes a system that determines (206), by one or more processors and based on the complex scattering coefficient, a statistical profile of a complex scattering magnitude over a second spectrum of microwave frequencies. In some implementations, the one or more processors are communicatively coupled to the network analyzer and receive the output signals that correspond to the scattering parameters (e.g., $S_{11}$, $S_{12}$, $S_{21}$, and $S_{22}$). The one or more processors compute a complex scattering magnitude for each frequency of a second spectrum of frequencies. In some cases, the complex scattering magnitude for each frequency of the second spectrum of frequencies is an average of multiple measurements at each frequency. In some cases, a given complex scattering magnitude is calculated from a real part and an imaginary part of a respective complex scattering coefficient.

In some implementations, the second spectrum of frequencies is a subset of the first spectrum of frequencies as described in relation to generating (204) microwaves data. For example, the second spectrum of frequencies can be 2.9 GHz to 3.2 GHZ, which is a subset of the example of the first spectrum of frequencies. In other words, the network analyzer determines scattering parameters over a broad range of microwave frequencies (e.g., the first spectrum of frequencies), and the one or more processors perform one or more analyses over a subset of the broad range of microwave frequencies (e.g., the second spectrum of frequencies), in accordance with one or more heuristics indicative of optimal conditions for executing the process 200.

One or more heuristics can help determine the second spectrum of microwave frequencies over which the one or more processors determine the statistical profile. In some implementations, the method for identifying the second spectrum of microwave frequencies is to consider the transmission spectrum and to choose the frequency range with a low and flat amplitude. In some other implementations, a high reflectance (e.g., determined by a measurement of S11 and/or S22 as a function of microwave frequency) can be indicative of an environment with high water content which, in some cases, is not a preferable environment to execute this method, as the magnitude of the transmission parameter can identify a presence of gas. Other examples use alternative heuristic measurements that indicate the second spectrum of microwave frequencies that is correlated with an optimal environment to execute the method of detecting increasing gas volume in a fluid.

In some implementations, the one or more processors determine a complex scattering magnitude for each complex scattering coefficient measured by the network analyzer. The complex scattering magnitude is the magnitude of a corresponding complex number. For example, the complex scattering magnitude of a complex scattering coefficient s=a+ib is $|s|=\sqrt{a^2+b^2}$. In some implementations, a controller configures the network analyzer to measure a complex scattering coefficient as a function of frequency over the first spectrum of frequencies. This yields a distribution of complex scattering coefficients $s(\omega_1)=a(\omega_1)+ib(\omega_1)$ evaluated over the first spectrum of frequencies ($\omega_1$) and a corresponding distribution of complex scattering magnitudes $|s(\omega_2)|=\sqrt{a(\omega_2)^2+b(\omega_2)^2}$ evaluated over the second spectrum of frequencies ($\omega_2$).

In some implementations, the one or more processors determine a statistical profile of the distribution of complex scattering magnitudes. For example, the one or more processors can arrange the complex scattering magnitudes in a histogram, in which multiple bins of complex scattering magnitudes are determined. Each bin is a subdivision of the full range of values of the complex scattering magnitudes. For example, if the full range of complex scattering magnitudes is between 0 and 100, the full range can be subdivided into 1,000 bins in which each bin represents 0.1 units of complex scattering magnitude. The histogram represents a distribution of counts of a number of measurements associated with a complex scattering magnitudes across the second spectrum of frequencies in each complex scattering magnitude bin.

As an illustrative example, consider a case in which the one or more processors determine a complex scattering magnitude at 50 frequencies within the second spectrum of frequencies. At each frequency, 100 measurements are collected from the network analyzer and associated processors. A data structure that includes 50 rows and 100 columns can be converted to a one-dimensional vector with 5,000 rows and 1 column. The one or more processors can determine a statistical profile (e.g., a histogram) based on the one-dimensional vector of complex scattering magnitudes.

Other examples of statistical profiles of the microwave data (e.g., the distribution of complex scattering magnitudes) can be determined by the one or more processors. For example, the one or more processors can determine a histogram of complex scattering magnitudes as a function of microwave frequency (e.g., the full range of microwave frequencies subdivided into frequency bins).

In some implementations, the one or more processors can determine an aggregate value of the statistical profile of complex scattering magnitudes. The aggregate value can be a particular parameter that describes the shape, range, dynamics, or any other property of the profile. For example, an average value of a statistical profile can be considered an aggregate value. As another example, a variance, standard deviation, and skewness represent shape characteristics of the statistical profile. As another example, a bimodality coefficient can be determined that is indicative of whether a statistical profile is bimodal. A bimodal statistical profile is a profile with two primary peaks. As the bimodality coefficient of a statistical profile increases, a degree of differentiation between two discrete peaks increases.

In some implementations, the one or more processors can monitor the aggregate value (e.g., the bimodality coefficient) over time to infer one or more dynamic properties of the fluid in the pipe.

The process 200 includes a system that determines (208), by the one or more processors and based on the statistical profile, that an amount of gas within the fluid of the pipe satisfies a threshold amount. In some implementations, the one or more processors use the bimodality coefficient of the statistical profile described in relation to step 206 (e.g., the histogram of complex scattering magnitudes) to determine an estimated amount of gas present within the pipe, and whether the amount satisfies a threshold amount. A predetermined relationship between the bimodality coefficient of the statistical profile and a GVF can be used to estimate an amount of gas in the pipe. Further discussion in relation to the correlation between the bimodality coefficient and the GVF of fluid in the pipe is provided in relation to the figures below.

In some implementations, a particular aggregate value of the statistical profile can correlate with one or more properties of the fluid in the pipe. For example, in some implementations that may depend on a specific composition of the fluid in the pipe, environmental factors, and/or the microwave frequency range, a bimodality coefficient of the statistical profile described in relation to determining (206) is indicative of an amount of gas present in the fluid of the pipe.

In some implementations, the process 200 includes a system that generates (210), based on the determination that an amount of gas within the pipe satisfies a threshold amount, an alert for field personnel specifying that the amount of gas within the pipe satisfies the threshold amount. For example, a bimodality coefficient of 0.6 or higher, which correlates with a GVF of 5% can initiate one or more alerts.

In some implementations, the process 200 includes a system that causes (212) a flow of fluid within the pipe to slow or stop until the amount of gas falls below a predetermined threshold. For example, an automatic shut off valve can stop the flow of fluids. As another example, a modification of the mud composition in the pipe can help mitigate gas intrusion.

Figure 3:
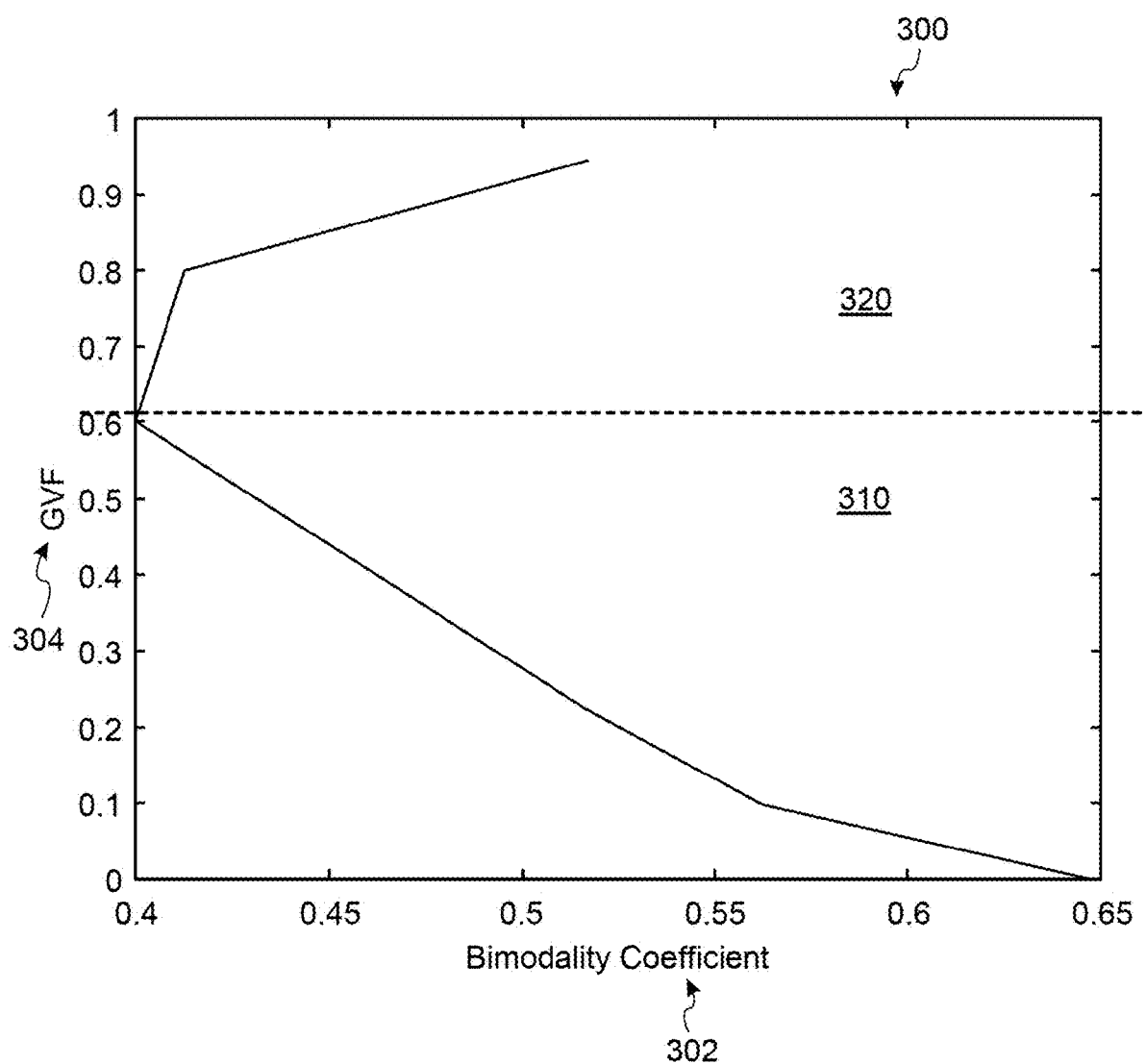
FIG. 3 is a plot that illustrates a relationship between a bimodality coefficient of a statistical profile of complex scattering magnitudes and a gas volume fraction (GVF).

FIG. 3 is a plot 300 that illustrates a relationship between a bimodality coefficient of a histogram of complex scattering magnitudes and a GVF. The one or more processors (e.g., the processor 160) receive signals (e.g., voltages) from multiple ports of a network analyzer (e.g., the network analyzer 140). In the system used to generate the data that illustrates the relationship in FIG. 3, the one or more processors determine a bimodality coefficient of the histogram, where the histogram represents a distribution of the complex scattering magnitudes across multiple complex scattering magnitude bins over a full range of a second frequency range (e.g., a frequency range that is a subset of a first frequency range).

The horizontal axis 302 of the plot 300 represents the bimodality coefficient of a particular histogram. The range of the particular bimodality coefficient is between 0.4 and 0.65. In general, as a bimodality coefficient increases, a corresponding distribution becomes more bimodal. In the limit of a distribution that includes two completely non-overlapping points, a corresponding bimodality coefficient is 1.

Two aggregate values of a particular statistical profile determine the bimodality coefficient. In particular, a bimodality coefficient is determined by a skewness (S) of a statistical profile and a kurtosis (K) of a statistical profile. The relationship between the three values can be written as $$b = (S^2 + 1) \bigg/ \left( K + \frac{3(N-1)^2}{(N-2)(N-3)} \right).$$

The skewness of a statistical profile can be written as $$S = \frac{\frac{1}{N}\sum_{i=1}^{N}(x_i - \bar{x})^3}{\left(\sqrt{\frac{1}{N}\sum_{i=1}^{N}(x_i - \bar{x})^2}\right)^3},$$

and the kurtosis with non-bias correction can be written as $$K = \frac{\frac{1}{N}\sum_{i=1}^{N}(x_i - \bar{x})^4}{\left(\sqrt{\frac{1}{N}\sum_{i=1}^{N}(x_i - \bar{x})^2}\right)^2},$$

where b is the bimodality coefficient, N is the number of elements in the statistical profile (e.g., the number of bins), $x_i$ is the value represented by the $i^{th}$ element of the N elements of the statistical profile, and $\bar{x}$ is the average value of the elements of the statistical profile. Kurtosis with non-bias correction represents a kurtosis measure of an entire population, rather than a sub-population. A kurtosis of a statistical profile represents how concentrated the values of a statistical profile are around a mean and can be used to determine if a statistical profile is normal or abnormally shaped. A skewness of a statistical profile is a measure of how asymmetric the statistical profile is around its mean. A statistical profile is asymmetric when its left and right sides are not mirror images. Skewness can be positive, negative, zero, or undefined.

The plot 300 illustrates a relationship between a bimodality coefficient of a particular statistical profile and a GVF of a particular fluid flowing through a pipe. The GVF is a ratio of the gas volumetric flow rate to the total volumetric flow rate of all fluids in the pipe. In other words, if all of the fluid flowing in a pipe is gaseous, the corresponding GVF is 1. Alternatively, if all of the fluid flowing in a pipe is liquid, the corresponding GVF is 0. Any intermediate mixture of liquid and gas demonstrates a GVF between 0 and 1.

The plot 300 is segmented into two vertical sections. A first section 310 corresponds to a range of GVF between 0 and 0.6. The second section corresponds to a range of GVF greater than 0.6. Considering the first section 310, as the bimodality coefficient (represented by the horizontal axis 302) increases from 0.4 to 0.65, the corresponding GVF decreases from 0.6 to 0. In other words, the particular statistical profile exhibits at least two peaks (e.g., local maxima), and as the distance between the peaks increases, a corresponding decrease in the GVF is observed. Similarly, as the statistical profile becomes less bimodal (e.g., the bimodality coefficient decreases), the corresponding increase in the GVF is observed. Further discussion of the shapes and dependence of the bimodal coefficient on the GVF is provided in relation to the following figures.

Considering the second section 320, higher ranges of GVF correlate with a decreasing bimodality coefficient. In other words, for GVF above 0.6, the corresponding bimodality coefficient decreases, which introduces an uncertainty in the evaluation of GVF when there are two possible values of GVF for a single bimodality coefficient. For example, a bimodality coefficient of 0.5 correlates with a GVF of approximately 0.3 or 0.9. This restriction results in a range of operability for this particular technique of GVF less than 0.6, where a one-to-one relationship between the bimodality coefficient and the GVF is achieved. In some implementations, the described technique is best suited for early detection (e.g., low GVF) of gas in a mud return pipe.

Figure 4:
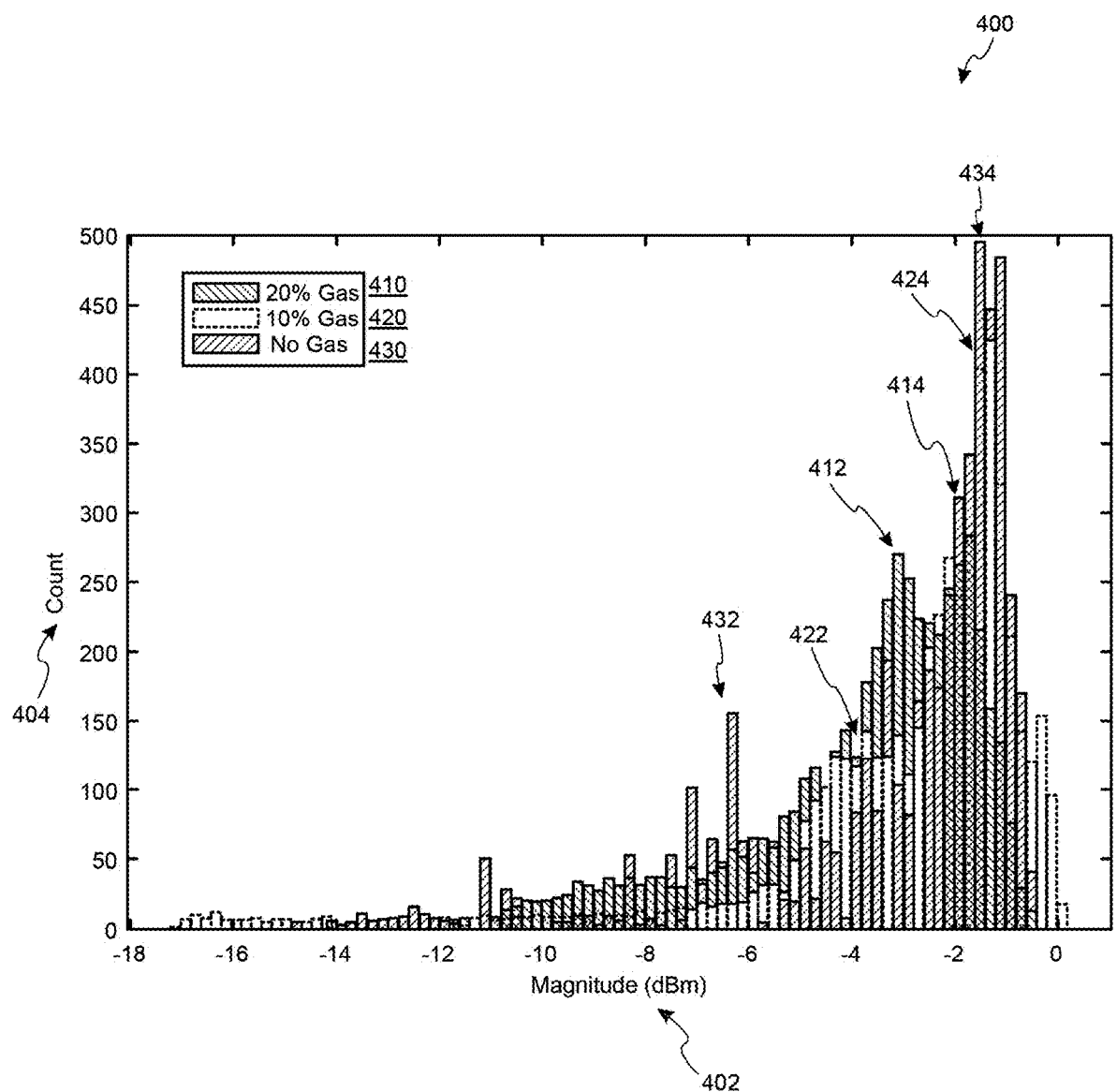
FIG. 4 is a plot of multiple statistical profiles.

FIG. 4 is a plot 400 of multiple statistical profiles, in which each statistical profile corresponds to a flow of fluid with a particular GVF in a commercial flow loop device configured for steady flow over a two minute interval, which simulates an environment that is observed in the field with a pipe (e.g., a hydrocarbon production pipe or a mud return pipe during drilling into a reservoir). A first statistical profile 410 represents a flow of fluid with a GVF of 0.2 (e.g., 20% gas volumetric flow rate). A second statistical profile 420 represents a flow of fluid with a GVF of 0.1 (e.g., 10% gas volumetric flow rate). A third statistical profile 430 represents a flow of fluid with a GVF of 0.0 (e.g., 0% gas volumetric flow rate).

A horizontal axis 402 of plot 400 represents complex scattering magnitude bins, as described in relation to FIG. 2. In this example, the particular complex scattering magnitude is a complex transmission magnitude, where a transmission power, expressed in units of dBm, is measured from the waveguide 120a to the waveguide 120b in reference to FIG. 1. The full range of complex transmission magnitudes is approximately 0 dBm to −18 dBm. Each bin corresponds to a subdivision of the full range of approximately 0.2 dBm (e.g., each dBm of complex transmission magnitude is divided into five bins).

A vertical axis 404 of plot 400 represents a count of measurements that result in a complex transmission magnitude in each particular complex transmission magnitude bin. For example, the first statistical profile 410 demonstrates approximately 260 measurements of complex transmission magnitudes that fell in the bin corresponding to −3.1 dBm (peak 412).

The first statistical profile 410 exhibits a first peak 412 and a second peak 414 with a separation of approximately 1.3 dBm. The second statistical profile 420 exhibits a first peak 422 and a second peak 424 with a separation of approximately 2.6 dBm. The third statistical profile 430 exhibits a first peak 432 and a second peak 434 with a separation of approximately 4.6 dBm. A trend of increasing peak separation decreasing GVF matches the data represented by the plot 300, in which a decrease in GVF correlates with an increase in the bimodality coefficient, which is consistent with a statistical profile exhibiting more distinct pairs of peaks (more bimodal) as GVF decreases.

In some cases, a sudden influx of gas in an OBM results in a formation of small gas bubbles that create reflection losses due to the spatially dependent permittivity from the bubbles. One or more processors can monitor a reduction of the maximum value of a particular statistical profile to determine a potential influx of gas bubbles which can lead to a potential gas kick. As the gas bubbles form, the peak value of the statistical profile can decrease and/or shift to the left. As the gas continues to intrude, the gas bubbles diminish in favor of a more uniform gas distribution, which leads to a slower trend in the reduction of the statistical profile peak. The sensitivity to the formation of gas bubbles offers a mechanism for the early detection of gas intrusion.

Figure 5A:
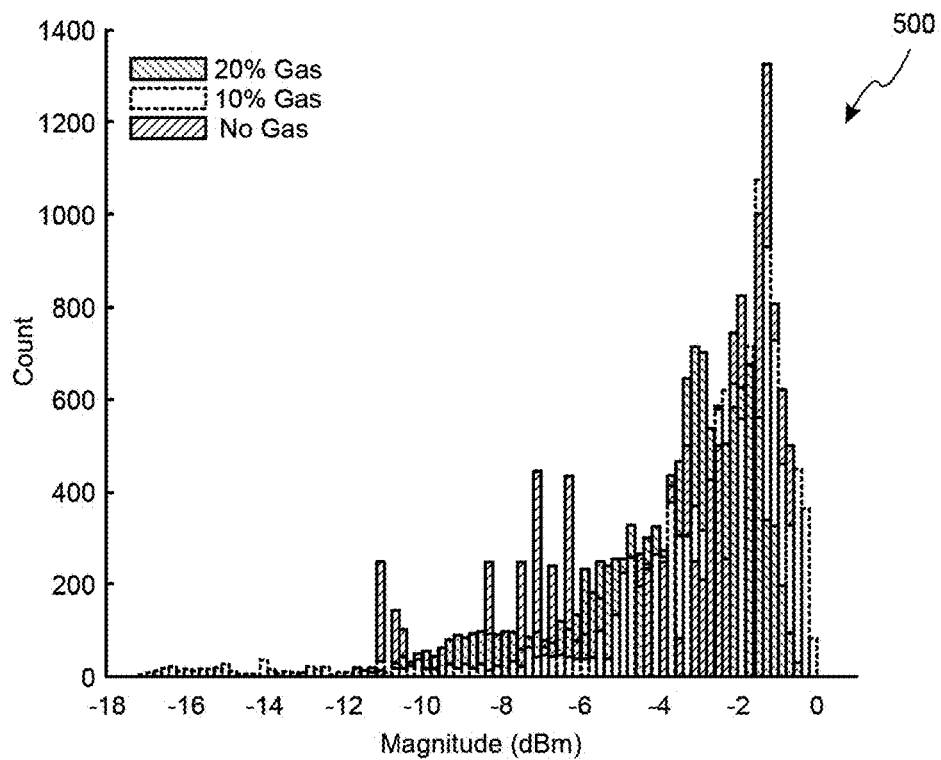
FIG. 5A is a plot of multiple statistical profiles.
Figure 5B:
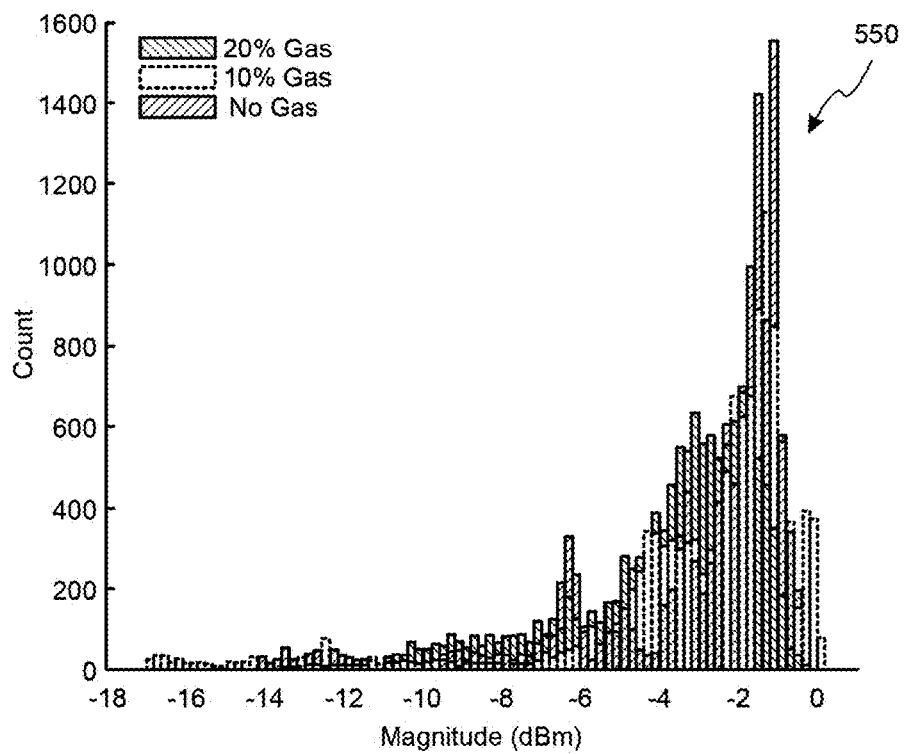
FIG. 5B is a plot of multiple statistical profiles.

FIG. 5A is a plot 500 of multiple statistical profiles, in which each statistical profile is associated with the statistical profiles described in relation to FIG. 4 for the first minute of the two minute interval. FIG. 5B is a plot 550 of multiple statistical profiles, in which each statistical profile is associated with the statistical profile described in relation to FIG. 4 for the second minute of the two minute interval. A comparison of plot 500 and plot 550 demonstrate a conserved distribution over time, in which a lower GVF exhibits a higher bimodality coefficient (e.g., peaks with more separation). Although certain aspects of the shape of each statistical distribution varies over time, an overall dependence on GVF on the statistical distribution is evident.

Figure 6:
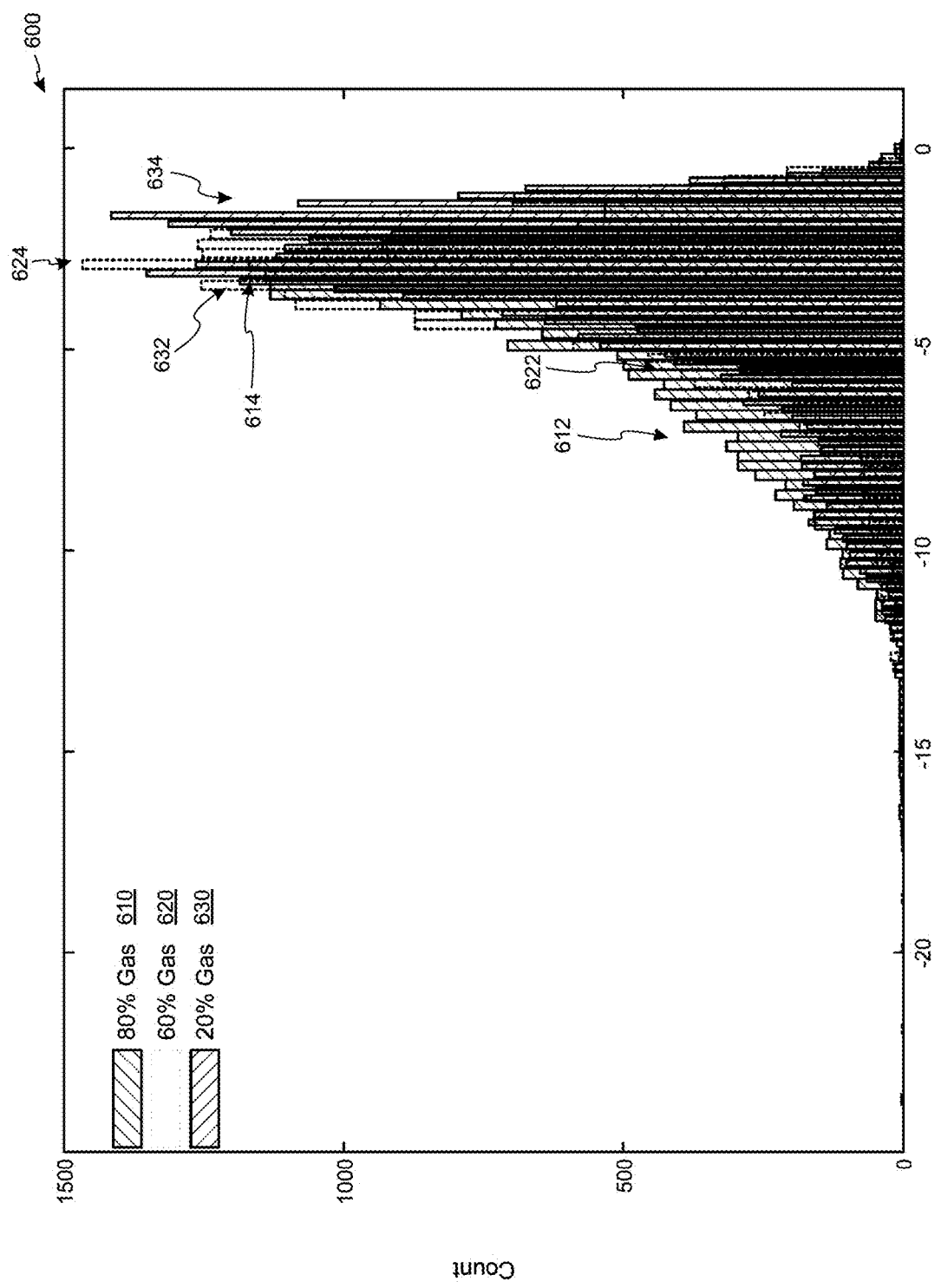
FIG. 6 is a plot of multiple statistical profiles.

FIG. 6 is a plot 600 of multiple statistical profiles, in which each statistical profile corresponds to a flow of fluid with a particular GVF in a commercial flow loop device configured for steady flow over a two minute interval, which simulates an environment that is observed in the field with a hydrocarbon production pipe or a mud return pipe during drilling. A first statistical profile 610 represents a flow of fluid with a GVF of 0.8 (e.g., 80% gas volumetric flow rate). A second statistical profile 620 represents a flow of fluid with a GVF of 0.6 (e.g., 60% gas volumetric flow rate). A third statistical profile 630 represents a flow of fluid with a GVF of 0.2 (e.g., 20% gas volumetric flow rate) which is also represented in plot 400 of FIG. 4.

The horizontal and vertical axes of plot 600 are the same as those described in relation to FIG. 4. The second statistical profile 620 represents the minimum bimodality coefficient in relation to FIG. 3. For example, a 0.6 GVF represents the separation between the first section 310 and the second section 320. In relation to plot 600, the second statistical profile 620 exhibits a primary peak (a second peak 624) and a secondary peak (a first peak 622), in which the first peak 622 and the second peak 624 have little separation. The small peak separation in relation to statistical profiles associated with different GVF is indicative of a smaller bimodality coefficient as illustrated in FIG. 3. As GVF increases, the second peak 624 becomes smaller and closer to the first peak 622.

As the GVF increases into the second section 320 (e.g., GVF of 0.8 associated with the first statistical profile 610), more separation is evident between a first peak 612 and a second peak 614, indicative of an increasing bimodality coefficient, which is illustrated in FIG. 3. In addition, the third statistical profile 630 exhibits a first peak 632 and a second peak 634 that are more distinct than both the first statistical profile 610 and the second statistical profile 620, which is expected in relation to the relationship illustrated by plot 300 of FIG. 3.

Figure 7:
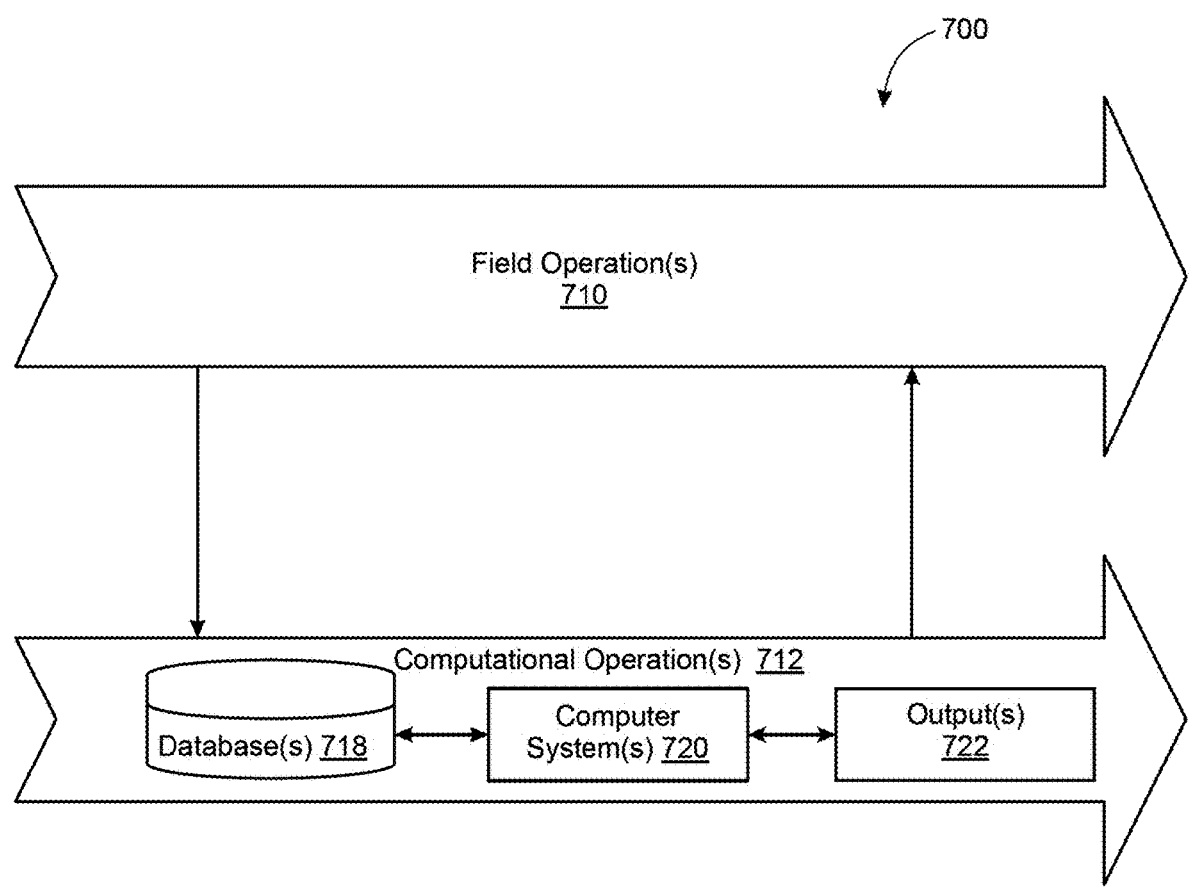
FIG. 7 is a schematic illustrating field operations to produce hydrocarbons.

FIG. 7 illustrates hydrocarbon production operations 700 that include both one or more field operations 710 and one or more computational operations 712, which exchange information and control exploration to produce hydrocarbons. In some implementations, outputs of techniques of the present disclosure (e.g., the method 200) can be performed before, during, or in combination with the hydrocarbon production operations 700, specifically, for example, either as field operations 710 or computational operations 712, or both. For example, the process 200 collect data during field operations, processes the data in computational operations, and can determine locations to perform additional field operations.

Examples of field operations 710 include forming/drilling a wellbore, hydraulic fracturing, producing through the wellbore, injecting fluids (such as water) through the wellbore, to name a few. In some implementations, methods of the present disclosure can trigger or control the field operations 710. For example, the methods of the present disclosure can generate data from hardware/software including sensors and physical data gathering equipment (e.g., seismic sensors, well logging tools, flow meters, and temperature and pressure sensors). The methods of the present disclosure can include transmitting the data from the hardware/software to the field operations 710 and responsively triggering the field operations 710 including, for example, generating plans and signals that provide feedback to and control physical components of the field operations 710. Alternatively, or in addition, the field operations 710 can trigger the methods of the present disclosure. For example, implementing physical components (including, for example, hardware, such as sensors) deployed in the field operations 710 can generate plans and signals that can be provided as input or feedback (or both) to the methods of the present disclosure.

Examples of computational operations 712 include one or more computer systems 720 that include one or more processors and computer-readable media (e.g., non-transitory computer-readable media) operatively coupled to the one or more processors to execute computer operations to perform the methods of the present disclosure. The computational operations 712 can be implemented using one or more databases 718, which store data received from the field operations 710 and/or generated internally within the computational operations 712 (e.g., by implementing the methods of the present disclosure) or both. For example, the one or more computer systems 720 process inputs from the field operations 710 to assess conditions in the physical world, the outputs of which are stored in the databases 718. For example, seismic sensors of the field operations 710 can be used to perform a seismic survey to map subterranean features, such as facies and faults. In performing a seismic survey, seismic sources (e.g., seismic vibrators or explosions) generate seismic waves that propagate in the earth and seismic receivers (e.g., geophones) measure reflections generated as the seismic waves interact with boundaries between layers of a subsurface formation. The source and received signals are provided to the computational operations 712 where they are stored in the databases 718 and analyzed by the one or more computer systems 720.

In some implementations, one or more outputs 722 generated by the one or more computer systems 720 can be provided as feedback/input to the field operations 710 (either as direct input or stored in the databases 718). The field operations 710 can use the feedback/input to control physical components used to perform the field operations 710 in the real world.

For example, the computational operations 712 can process the seismic data to generate three-dimensional (3D) maps of the subsurface formation. The computational operations 712 can use these 3D maps to provide plans for locating and drilling exploratory wells. In some operations, the exploratory wells are drilled using logging-while-drilling (LWD) techniques which incorporate logging tools into the drill string. LWD techniques can enable the computational operations 712 to process new information about the formation and control the drilling to adjust to the observed conditions in real-time.

The one or more computer systems 720 can update the 3D maps of the subsurface formation as information from one exploration well is received and the computational operations 712 can adjust the location of the next exploration well based on the updated 3D maps. Similarly, the data received from production operations can be used by the computational operations 712 to control components of the production operations. For example, production well and pipeline data can be analyzed to predict slugging in pipelines leading to a refinery and the computational operations 712 can control machine operated valves upstream of the refinery to reduce the likelihood of plant disruptions that run the risk of taking the plant offline.

In some implementations of the computational operations 712, customized user interfaces can present intermediate or final results of the above-described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or app), or at a central processing facility.

The presented information can include feedback, such as changes in parameters or processing inputs, that the user can select to improve a production environment, such as in the exploration, production, and/or testing of petrochemical processes or facilities. For example, the feedback can include parameters that, when selected by the user, can cause a change to, or an improvement in, drilling parameters (including drill bit speed and direction) or overall production of a gas or oil well. The feedback, when implemented by the user, can improve the speed and accuracy of calculations, streamline processes, improve models, and solve problems related to efficiency, performance, safety, reliability, costs, downtime, and the need for human interaction.

In some implementations, the feedback can be implemented in real-time, such as to provide an immediate or near-immediate change in operations or in a model. The term real-time (or similar terms as understood by one of ordinary skill in the art) means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 10 s. While the requested data need not be displayed (or initiated for display) instantaneously, it is displayed (or initiated for display) without any intentional delay, accounting for processing limitations of a described computing system and time required to, for example, gather, accurately measure, analyze, process, store, or transmit the data.

Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart or are in different countries or other jurisdictions.

Figure 8:
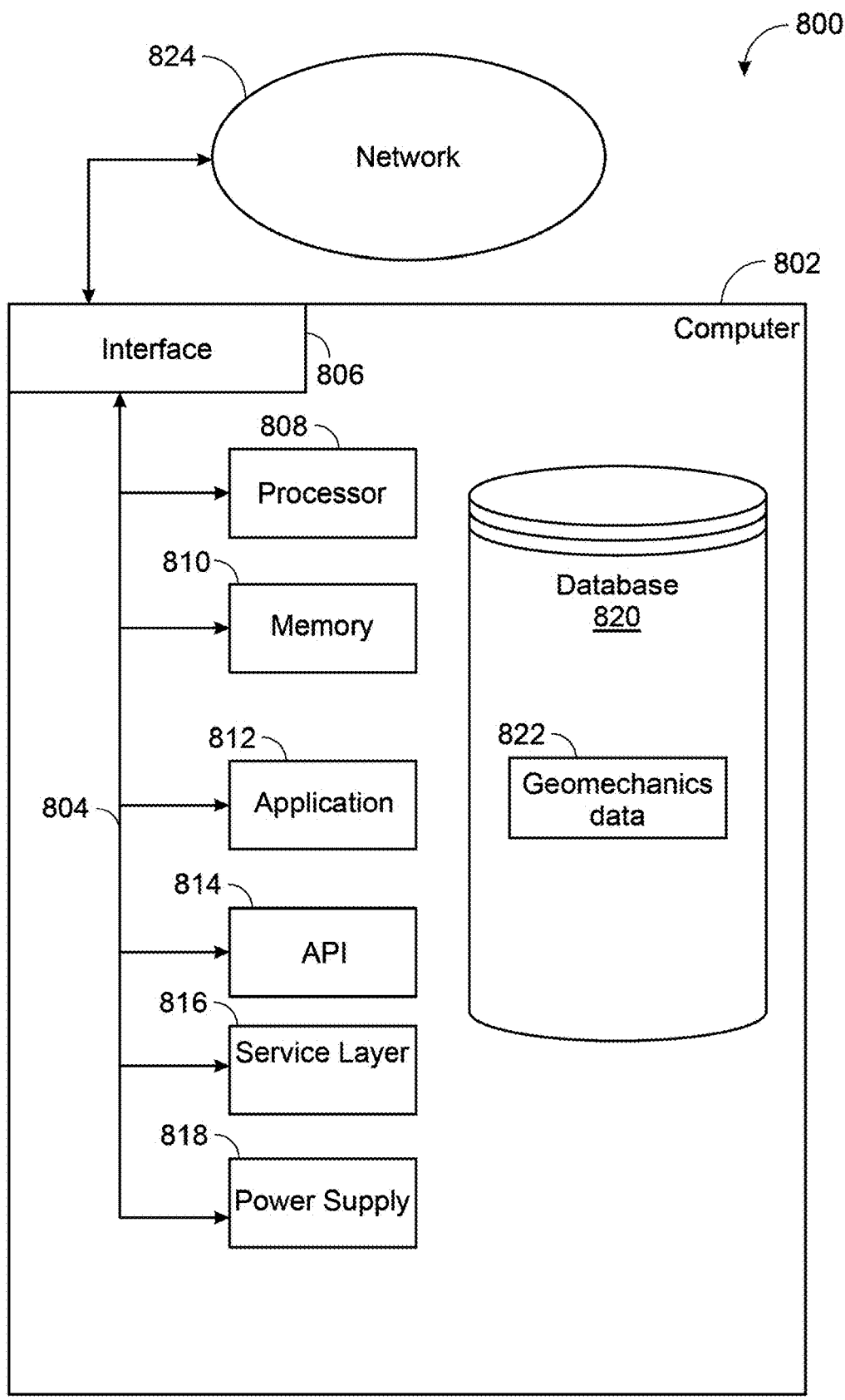
FIG. 8 is a diagram of an example computing system.

FIG. 8 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 824. In some implementations, one or more components of the computer 802 can be configured to operate within different environments, including cloud-computing-based environments, local environments, global environments, and combinations of environments.

At a high level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 824 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 804. In some implementations, any or all of the components of the computer 802, including hardware or software components, can interface with each other or the interface 806 (or a combination of both), over the system bus 804. Interfaces can use an application programming interface (API) 814, a service layer 816, or a combination of the API 814 and service layer 816. The API 814 can include specifications for routines, data structures, and object classes. The API 814 can be either computer-language independent or dependent. The API 814 can refer to a complete interface, a single function, or a set of APIs.

The service layer 816 can provide software services to the computer 802 and other components (whether illustrated or not) that are communicably coupled to the computer 802. The functionality of the computer 802 can be accessible for all service consumers using this service layer. Software services, such as those provided by the service layer 816, can provide reusable, defined functionalities through a defined interface. For example, the interface can be software written in JAVA, C++, or a language providing data in extensible markup language (XML) format. While illustrated as an integrated component of the computer 802, in alternative implementations, the API 814 or the service layer 816 can be stand-alone components in relation to other components of the computer 802 and other components communicably coupled to the computer 802. Moreover, any or all parts of the API 814 or the service layer 816 can be implemented as child or sub-modules of another software module, enterprise application, or hardware module without departing from the scope of the present disclosure.

The computer 802 includes an interface 806. Although illustrated as a single interface 806 in FIG. 8, two or more interfaces 806 can be used according to implementations of the computer 802 and the described functionality. The interface 806 can be used by the computer 802 for communicating with other systems that are connected to the network 824 (whether illustrated or not) in a distributed environment. Generally, the interface 806 can include, or be implemented using, logic encoded in software or hardware (or a combination of software and hardware) operable to communicate with the network 824. More specifically, the interface 806 can include software supporting one or more communication protocols associated with communications. As such, the network 824 or the interface's hardware can be operable to communicate physical signals within and outside of the illustrated computer 802.

The computer 802 includes a processor 808. Although illustrated as a single processor 808 in FIG. 8, two or more processors 808 can be used according to implementations of the computer 802 and the described functionality. Generally, the processor 808 can execute instructions and can manipulate data to perform the operations of the computer 802, including operations using algorithms, methods, functions, processes, flows, and procedures as described in the present disclosure.

The computer 802 also includes a database 820 that can hold data (such geomechanics data 822) for the computer 802 and other components connected to the network 824 (whether illustrated or not). For example, database 820 can be in-memory or a database storing data consistent with the present disclosure. In some implementations, database 820 can be a combination of two or more different database types (for example, hybrid in-memory and conventional databases) according to implementations of the computer 802 and the described functionality. Although illustrated as a single database 820 in FIG. 8, two or more databases (of the same, different, or combination of types) can be used according to implementations of the computer 802 and the described functionality. While database 820 is illustrated as an internal component of the computer 802, in alternative implementations, database 820 can be external to the computer 802.

The computer 802 also includes a memory 810 that can hold data for the computer 802 or a combination of components connected to the network 824 (whether illustrated or not). Memory 810 can store any data consistent with the present disclosure. In some implementations, memory 810 can be a combination of two or more different types of memory (for example, a combination of semiconductor and magnetic storage) according to implementations of the computer 802 and the described functionality. Although illustrated as a single memory 810 in FIG. 8, two or more memories 810 (of the same, different, or combination of types) can be used according to implementations of the computer 802 and the described functionality. While memory 810 is illustrated as an internal component of the computer 802, in alternative implementations, memory 810 can be external to the computer 802.

The application 812 can be an algorithmic software engine providing functionality according to implementations of the computer 802 and the described functionality. For example, application 812 can serve as one or more components, modules, or applications. Further, although illustrated as a single application 812, the application 812 can be implemented as multiple applications 818 on the computer 802. In addition, although illustrated as internal to the computer 802, in alternative implementations, the application 812 can be external to the computer 802.

The computer 802 can also include a power supply 818. The power supply 818 can include a rechargeable or non-rechargeable battery that can be configured to be either user- or non-user-replaceable. In some implementations, the power supply 818 can include power-conversion and management circuits, including recharging, standby, and power management functionalities. In some implementations, the power-supply 818 can include a power plug to allow the computer 802 to be plugged into a wall socket or a power source to, for example, power the computer 802 or recharge a rechargeable battery.

There can be any number of computers 802 associated with, or external to, a computer system including the computer 802, with each computer 802 communicating over network 824. Further, the terms "client," "user," and other appropriate terminology can be used interchangeably, as appropriate, without departing from the scope of the present disclosure. Moreover, the present disclosure contemplates that many users can use one computer 802 and one user can use multiple computers 802.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random-access memory (RAM), read only memory (ROM), phase change memory (PRAM), static random-access memory (SRAM), dynamic random-access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks.

While this specification contains many specific implementation details, these should not be construed as limitations on the scope of what may be claimed, but rather as descriptions of features that may be specific to implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Several implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

Several embodiments of these systems and methods have been described. Nevertheless, it will be understood that various modifications may be made without departing from the spirit and scope of this disclosure. Accordingly, other embodiments are within the scope of the following claims.

Examples

In some implementations, methods of detecting an increase in gas content in a fluid flowing through a pipe include (i) flowing fluid through a pipe, (ii) generating, by a network analyzer, microwaves data representing a complex scattering coefficient of microwaves over a first spectrum of microwave frequencies, in which the microwaves are emitted through a waveguide and the fluid within the pipe, (iii) determining, by one or more processors and based on the complex scattering coefficient, a statistical profile of a complex scattering magnitude over a second spectrum of microwave frequencies, (iv) determining, by the one or more processors and based on the statistical profile, that an amount of gas within the pipe satisfies a threshold amount, and (v) causing a flow of fluid within the pipe to slow or stop until the amount of gas falls below a predetermined threshold value.

In an example implementation combinable with any other implementation, the statistical profile is indicative of a presence of gas bubbles within the fluid.

In an example implementation combinable with any other implementation, the pipe is a hydrocarbon production pipe or a drilling mud return pipe.

In an example implementation combinable with any other implementation, the second spectrum of microwave frequencies is a subset of the first spectrum of microwave frequencies.

In an example implementation combinable with any other implementation, determining the statistical profile includes (i) determining, by the one or more processors, a distribution of the complex scattering magnitude across a plurality of complex scattering magnitude bins, in which each complex scattering magnitude bin is a subdivision of the full range of magnitudes associated with the complex scattering magnitudes, and (ii) determining, by the one or more processors, a bimodality coefficient of the distribution.

In an example implementation combinable with any other implementation, the waveguide comprises a first dielectric waveguide positioned on a first side of the pipe and a second dielectric waveguide positioned on a second side of the pipe.

In an example implementation combinable with any other implementation, measuring the complex scattering coefficient associated with the fluid within the pipe includes averaging a plurality of measurements.

In an example implementation combinable with any other implementation, a given complex scattering coefficient is indicative of reflection or transmission.

In an example implementation combinable with any other implementation, a complex scattering magnitude is calculated from a real part and an imaginary part of a respective complex scattering coefficient.

In an example implementation combinable with any other implementation, the waveguide is a dielectrically-filled waveguide.

In some implementations, methods of detecting an increase in gas content in a pipe include (i) generating, by a network analyzer, microwaves data representing a complex scattering coefficient of microwaves over a first spectrum of microwave frequencies, in which the microwaves are emitted through a waveguide and fluid within the pipe, (ii) determining, by one or more processors and based on the complex scattering coefficient, a statistical profile of a complex scattering magnitude over a second spectrum of microwave frequencies, (iii) determining, by the one or more processors and based on the statistical profile, that an amount of gas within the pipe satisfies a threshold amount, and (iv) generating, based on the determining, an alert for field personnel specifying that the amount of gas within the pipe satisfies the threshold amount.

In an example implementation combinable with any other implementation, the method includes responsive to generating the alert, causing flow of fluid within the pipe to slow or stop until the amount of gas falls below a predetermined threshold value.

In an example implementation combinable with any other implementation, the statistical profile is indicative of a presence of gas bubbles within the fluid.

In an example implementation combinable with any other implementation, determining the statistical profile includes (i) determining, by the one or more processors, a distribution of the complex scattering magnitude across a plurality of complex scattering magnitude bins, wherein each complex scattering magnitude bin is a subdivision of the full range of magnitudes associated with the complex scattering magnitudes, and (ii) determining, by the one or more processors, a bimodality coefficient of the distribution.

In an example implementation combinable with any other implementation, the waveguide comprises a first dielectric waveguide positioned on a first side of the pipe and a second dielectric waveguide positioned on a second side of the pipe.

In an example implementation combinable with any other implementation, measuring the complex scattering coefficients associated with the fluid within the pipe includes averaging a plurality of measurements.

In an example implementation combinable with any other implementation, a given complex scattering coefficient includes a complex transmission coefficient or a complex reflection coefficient.

In an example implementation combinable with any other implementation, a complex scattering magnitude is calculated from a real part and an imaginary part of a respective complex scattering coefficient.

In some implementations, systems for detecting an increase in gas content in a pipe include a waveguide, wherein the waveguide includes (i) a first waveguide attached to the pipe, the first waveguide configured to direct a microwave to a fluid in the pipe, and (ii) a second waveguide attached to the pipe, the second waveguide configured to receive a microwave that propagates through the fluid in the pipe, a network analyzer connected with the first waveguide, wherein the network analyzer is configured to transmit the microwaves to the first waveguide, receive the microwaves from the second waveguide, the microwaves transmitted through the fluid, and obtain measurement results based on the transmitted microwaves, wherein the measurement results are used to determine an increase in gas content in the pipe.

In an example implementation combinable with any other implementation, detecting an increase in gas content in a pipe includes a processor communicatively coupled with the network analyzer, in which the processor includes a memory and at least one hardware processor communicatively coupled with the memory and configured to determine an increase in gas content in the pipe based on the measurement results.

What is claimed is:

1. A method of detecting an increase in gas content in a fluid flowing through a pipe, the method comprising:
 flowing fluid through a pipe;
 generating, by a network analyzer, microwaves data representing a complex scattering coefficient of microwaves over a first spectrum of microwave frequencies, wherein the microwaves are emitted through a waveguide and the fluid within the pipe;
 determining, by one or more processors and based on the complex scattering coefficient, a statistical profile of a complex scattering magnitude over a second spectrum of microwave frequencies;
 determining, by the one or more processors and based on the statistical profile, that an amount of gas within the pipe satisfies a threshold amount; and
 causing a flow of fluid within the pipe to slow or stop until the amount of gas falls below a predetermined threshold value.

2. The method of claim 1, wherein the statistical profile is indicative of a presence of gas bubbles within the fluid.

3. The method of claim 1, wherein the pipe is a hydrocarbon production pipe or a drilling mud return pipe.

4. The method of claim 1, wherein the second spectrum of microwave frequencies is a subset of the first spectrum of microwave frequencies.

5. The method of claim 1, wherein determining the statistical profile comprises: (i) determining, by the one or more processors, a distribution of the complex scattering magnitude across a plurality of complex scattering magnitude bins, wherein each complex scattering magnitude bin is a subdivision of a full range of magnitudes associated with the complex scattering magnitudes, and (ii) determining, by the one or more processors, a bimodality coefficient of the distribution.

6. The method of claim 1, wherein the waveguide comprises a first dielectric waveguide positioned on a first side of the pipe and a second dielectric waveguide positioned on a second side of the pipe.

7. The method of claim 1, wherein measuring the complex scattering coefficient associated with the fluid within the pipe includes averaging a plurality of measurements.

8. The method of claim 1, wherein a given complex scattering coefficient is indicative of reflection or transmission.

9. The method of claim 1, wherein a complex scattering magnitude is calculated from a real part and an imaginary part of a respective complex scattering coefficient.

10. The method of claim 1, wherein the waveguide is a dielectrically-filled waveguide.

11. A method of detecting an increase in gas content in a pipe, the method comprising:
 generating, by a network analyzer, microwaves data representing a complex scattering coefficient of microwaves over a first spectrum of microwave frequencies, wherein the microwaves are emitted through a waveguide and fluid within the pipe;
 determining, by one or more processors and based on the complex scattering coefficient, a statistical profile of a complex scattering magnitude over a second spectrum of microwave frequencies;
 determining, by the one or more processors and based on the statistical profile, that an amount of gas within the pipe satisfies a threshold amount; and
 generating, based on the determining, an alert for field personnel specifying that the amount of gas within the pipe satisfies the threshold amount.

12. The method of claim 11, further comprising: responsive to generating the alert, causing flow of fluid within the pipe to slow or stop until the amount of gas falls below a predetermined threshold value.

13. The method of claim 11, wherein the statistical profile is indicative of a presence of gas bubbles within the fluid.

14. The method of claim 11, wherein determining the statistical profile comprises: (i) determining, by the one or more processors, a distribution of the complex scattering magnitude across a plurality of complex scattering magnitude bins, wherein each complex scattering magnitude bin is a subdivision of a full range of magnitudes associated with the complex scattering magnitudes, and (ii) determining, by the one or more processors, a bimodality coefficient of the distribution.

15. The method of claim 11, wherein the waveguide comprises a first dielectric waveguide positioned on a first side of the pipe and a second dielectric waveguide positioned on a second side of the pipe.

16. The method of claim 11, wherein measuring the complex scattering coefficients associated with the fluid within the pipe includes averaging a plurality of measurements.

17. The method of claim 11, wherein a given complex scattering coefficient includes a complex transmission coefficient or a complex reflection coefficient.

18. The method of claim 11, wherein a complex scattering magnitude is calculated from a real part and an imaginary part of a respective complex scattering coefficient.

19. A system for detecting an increase in gas content in a pipe, the system comprising:
 a waveguide, wherein the waveguide comprises: (i) a first waveguide attached to the pipe, the first waveguide configured to direct a microwave to a fluid in the pipe, and (ii) a second waveguide attached to the pipe, the second waveguide configured to receive a microwave that propagates through the fluid in the pipe;
 a network analyzer connected with the first waveguide, wherein the network analyzer is configured to:
 transmit the microwaves to the first waveguide;
 receive the microwaves from the second waveguide, the microwaves transmitted through the fluid; and
 obtain measurement results based on the transmitted microwaves, wherein the measurement results are used to determine an increase in gas content in the pipe, wherein the measurement results comprise microwaves data representing a complex scattering coefficient of the microwaves over a first spectrum of microwave frequencies.

20. The system of claim 19, further comprising a processor communicatively coupled with the network analyzer, wherein the processor comprises:
 a memory; and
 at least one hardware processor communicatively coupled with the memory and configured to determine: (i) a statistical profile of a complex scattering magnitude over a second spectrum of microwave frequencies, based on the complex scattering coefficient, and (ii) an increase in gas content in the pipe based on the measurement results and the statistical profile.

* * * * *